(12) United States Patent
Bush et al.

(10) Patent No.: US 7,582,762 B2
(45) Date of Patent: Sep. 1, 2009

(54) SALT AND CRYSTALLINE FORMS OF (2R)-ANTI-5-{3-[4-(10,11-DIFLUOROMETHANO-DIBENZOSUBER-5-YL)PIPERAZIN-1-YL]-2-HYDROXYPROPOXY}QUINOLINE

(75) Inventors: Julie Kay Bush, Fishers, IN (US); Susan Marie Reutzel-Edens, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 61 days.

(21) Appl. No.: 11/753,526

(22) Filed: May 24, 2007

(65) Prior Publication Data

US 2007/0244124 A1    Oct. 18, 2007

Related U.S. Application Data

(63) Continuation of application No. 10/471,443, filed as application No. PCT/US02/08256 on Apr. 12, 2002, now Pat. No. 7,282,585.

(60) Provisional application No. 60/318,815, filed on Sep. 13, 2001, provisional application No. 60/286,556, filed on Apr. 25, 2001.

(51) Int. Cl.
*A61K 31/50* (2006.01)
*C07D 487/00* (2006.01)

(52) U.S. Cl. .................. 544/363; 514/253.06

(58) Field of Classification Search ................. 544/363; 514/253.06

See application file for complete search history.

(56) References Cited

U.S. PATENT DOCUMENTS 5,654,304 A    8/1997    Slate et al.

FOREIGN PATENT DOCUMENTS

| WO | WO 00 75121 | 12/2000 |
|----|----|----|
| WO | WO 00 75132 | 12/2000 |

OTHER PUBLICATIONS

Leusen, "Ab initio prediction of polymorphs," Journal of Crystal Growth, North-Holland Publishing Co. Amsterdam, NL, vol. 166, No. 1, pp. 900-903 (1996) XP004053471.

Knapman, "Polymorph Prediction 2/2," The Alchemist Molmodelling, "Online!" (1999); XP002207460.

*Primary Examiner*—James O. Wilson
*Assistant Examiner*—Paul V. Ward
(74) *Attorney, Agent, or Firm*—Knobbe Martens Olson & Bear LLP

(57) ABSTRACT

The present invention provides methods of treating leukemia comprising administration of a resistance modulating amount of a compound having the formula (2r)-anti-5-{3-[4-(10,11-difluoromethano-dibenzosuber-5-yl)piperazin-1-yl]-2-hydroxypropoxy}quinoline 2.5 hydrochloride.

8 Claims, 4 Drawing Sheets

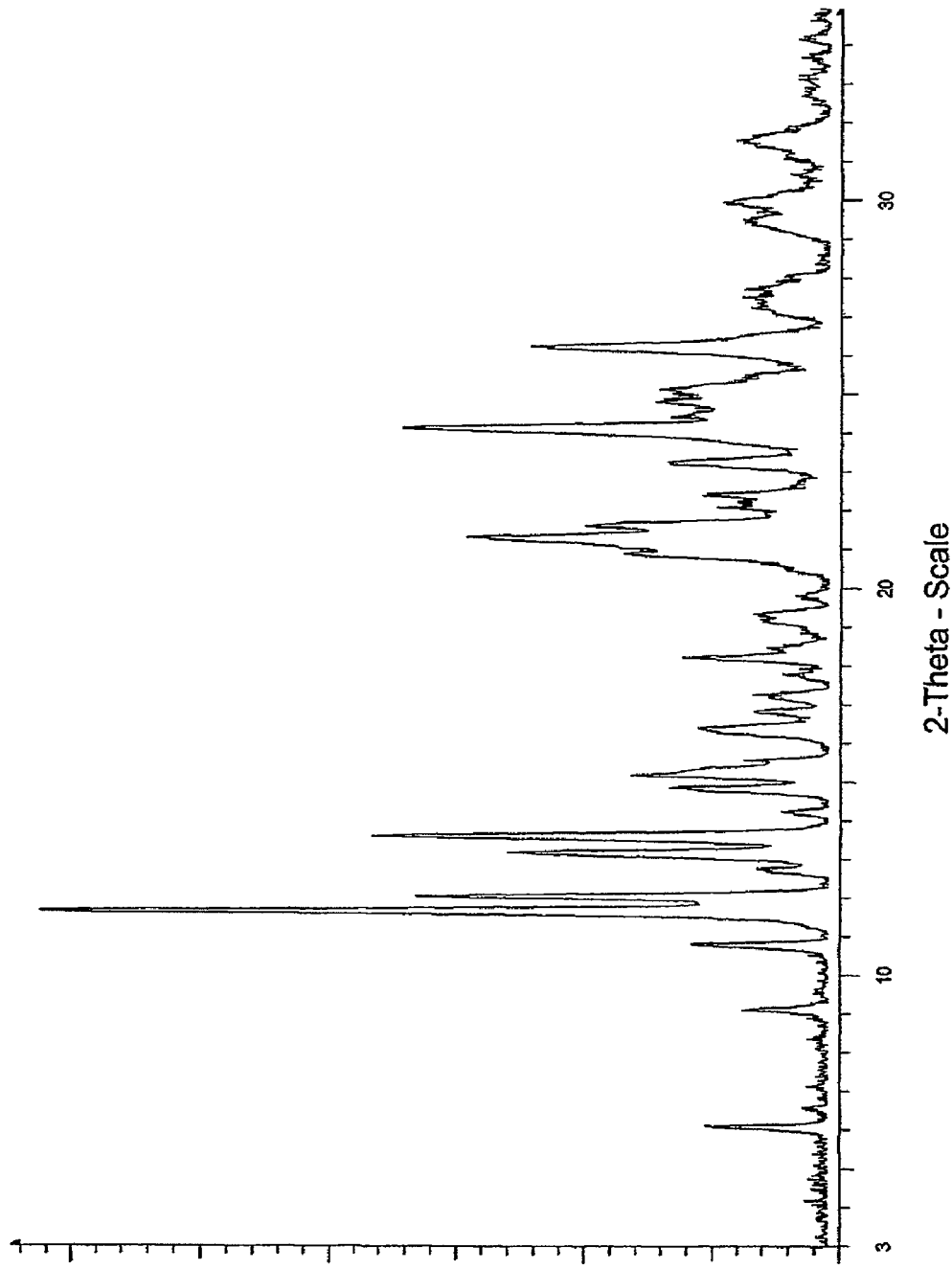
Figure 1 - X-ray powder diffraction pattern of Form II

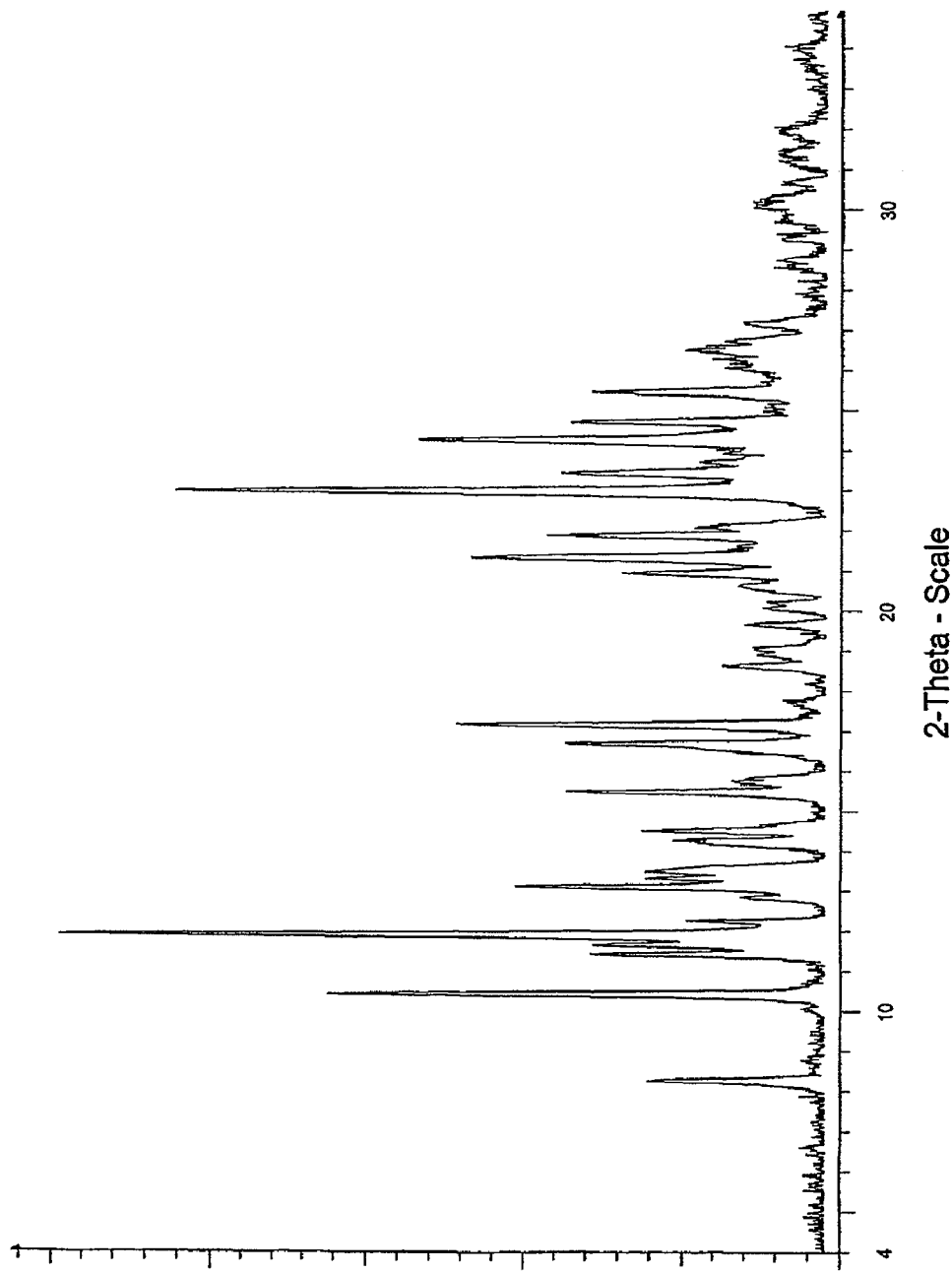
Figure 2 - X-ray powder diffraction pattern of Form III

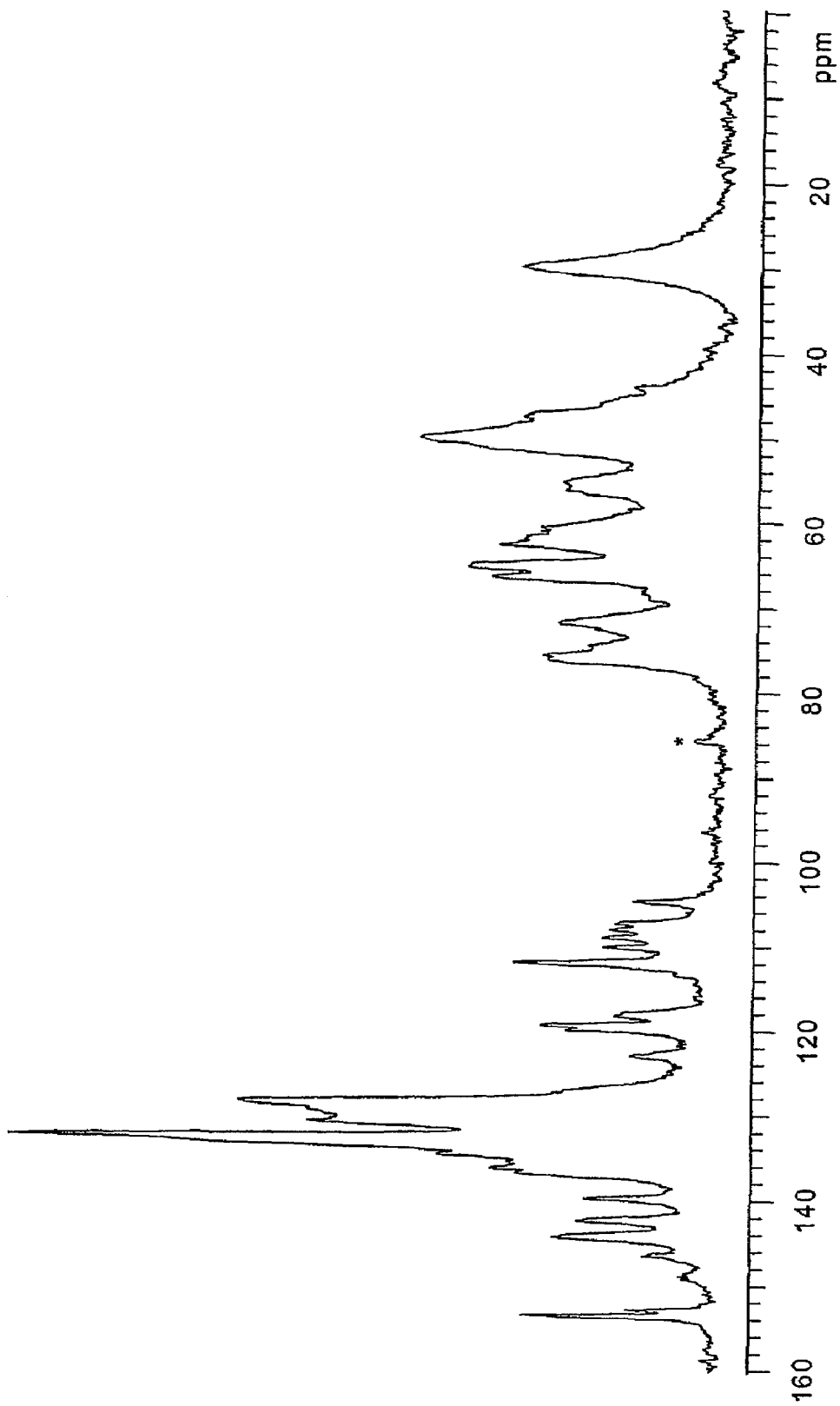

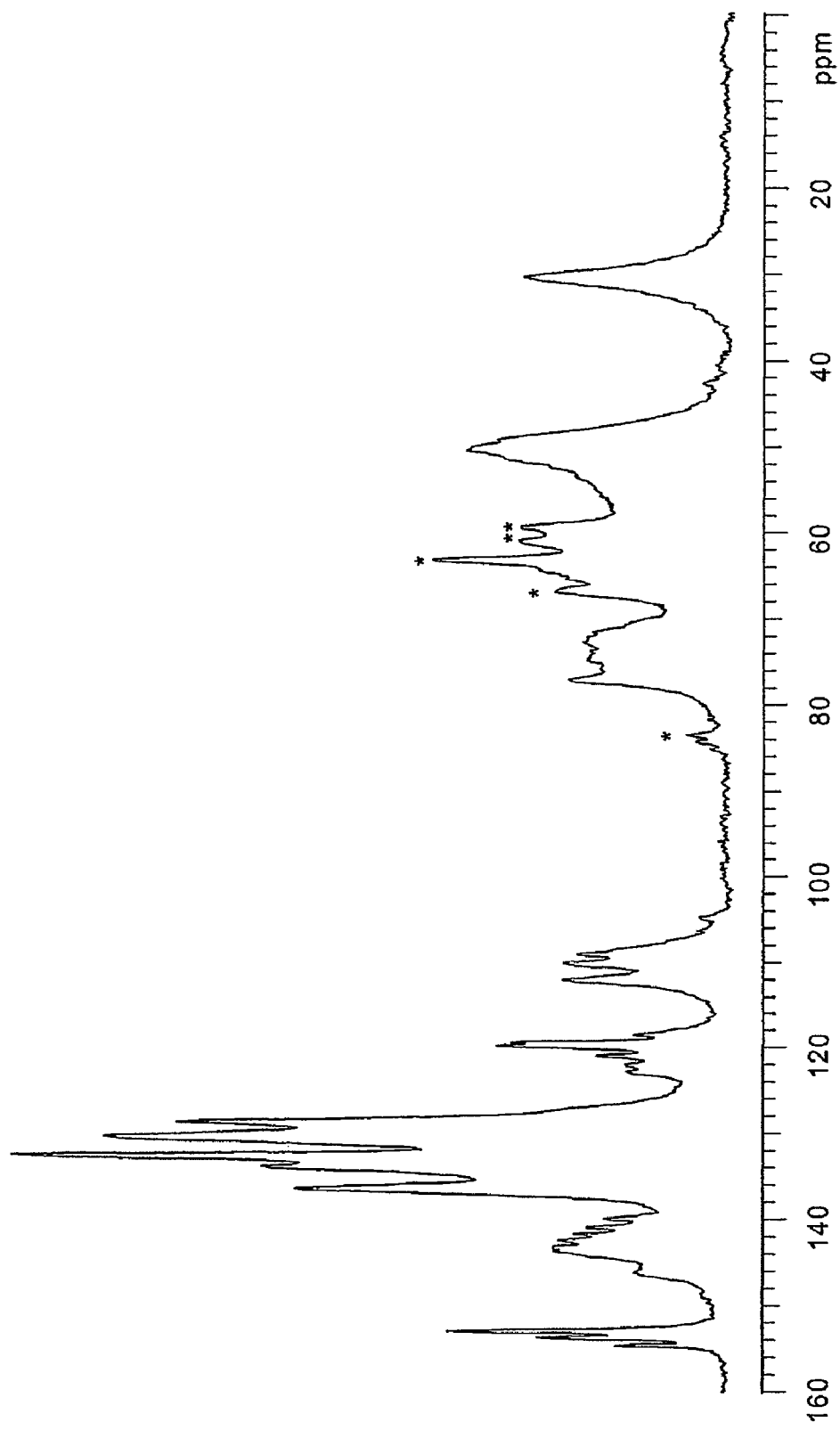
Figure 4 - $^{13}$C CP/MAS NMR spectrum of Form III. Asterisks (*) denote spinning sidebands.

SALT AND CRYSTALLINE FORMS OF (2R)-ANTI-5-{3-[4-(10,11-DIFLUOROMETHANO-DIBENZOSUBER-5-YL)PIPERAZIN-1-YL]-2-HYDROXYPROPOXY}QUINOLINE

CROSS REFERENCE TO RELATED APPLICATIONS

This application is a continuation of U.S. application Ser. No. 10/471,443 filed on Sep. 10, 2003 which is the US National Phase application of PCT/US02/08256, filed on Apr. 12, 2002, published as WO 02/087581 which claims priority to U.S. Provisional Application Nos.: 60/286,556 filed on Apr. 25, 2001 and 60/318,815 filed on Sep. 13, 2001 the entire disclosures of which are incorporated by reference in their entirety.

BACKGROUND OF THE INVENTION

Among the problems faced in certain types of drug therapy, including cancer chemotherapy and malaria drug therapy, is the phenomena of resistance to treatment regimens. The resistance means, for example, that cancerous tumors that responded well initially to a particular drug or drugs, later develop a tolerance to the drug(s). Drug resistance is the name given to the circumstance when a disease does not respond to a treatment drug or drugs. Drug resistance can be either intrinsic, which means the disease has never been responsive to the drug(s), or it can be acquired, which means the disease ceases responding to a drug or drugs to which the disease had previously been responsive. Multidrug resistance is a specific type of drug resistance that is characterized by cross-resistance of a disease to more than one functionally and/or structurally unrelated drugs. Multidrug resistance in the field of cancer, is discussed in greater detail in Kuzmich and Tew, "Detoxification Mechanisms and Tumor Cell Resistance to Anticancer Drugs," particularly section VII "The Multidrug-Resistant Phenotype (MDR)," *Medical Research Reviews*, Vol. 11, No. 2, 185-217, particularly 208-213 (1991); and in Georges, Sharom and Ling, "Multidrug Resistance and Chemosensitization: Therapeutic Implications for Cancer Chemotherapy," *Advances in Pharmacology*, Vol. 21, 185-220 (1990).

Treatment of drug and multidrug resistance typically involves the coadministration of a drug suitable for treatment of the disease and a compound which acts through various mechanisms to cause the drug suitable for treatment of a disease to begin and/or continue to function as a therapeutic agent.

U.S. Pat. No. 5,654,304 ('304), incorporated by reference herein, discloses a series of 10,11-(optionally substituted) methanodibenzosuberane derivatives useful in enhancing the efficacy of existing cancer chemotherapeutics and for treating multidrug resistance. (2R)-anti-5-{3-[4-(10,11-Difluoromethanodibenzosuber-5-yl)piperazin-1-yl]-2-hydroxypropoxy}quinoline trihydrochloride is disclosed in '304 and is currently under development as a pharmaceutical agent for the treatment of leukemia. WO00/75121 discloses Form I, a crystalline form of (2R)-anti-5-{3-[4-(10,11-difluoromethanodibenzosuber-5-yl)piperazin-1-yl]-2-hydroxypropoxy}quinoline trihydrochloride.

BRIEF SUMMARY OF THE INVENTION

There continues to be a need for novel salt and crystalline forms of (2R)-anti-5-{3-[4-(10,11-difluoromethanodibenzosuber-5-yl)piperazin-1-yl]-2-hydroxypropoxy}quinoline, which can be conveniently formulated for administration to patients and which are pure and highly crystalline in order to fulfill exacting pharmaceutical requirements and specifications. Preferably, such compounds will be readily formed and have favorable bulk characteristics. Examples of favorable bulk characteristics are drying times, filterability, solubility, intrinsic dissolution rate, thermal stability, and hygroscopicity. Decreased levels of organic solvents in the crystal lattice are also favorable, due in part to potential solvent toxicity to the recipient as a function of the solvent. Furthermore, the process for preparing such a compound also needs to be conveniently carried out on commercial scale.

We have now surprisingly and unexpectedly found one salt and two novel crystalline forms of (2R)-anti-5-{3-[4-(10,11-difluoromethanodibenzosuber-5-yl)piperazin-1-yl]-2-hydroxypropoxy}quinoline; (2R)-anti-5-{3-[4-(10,11-difluoromethanodibenzosuber-5-yl)piperazin-1-yl]-2-hydroxypropoxy}quinoline 2.5 hydrochloride and it's crystalline forms, Form II and Form III. The 2.5 salt and Form II and Form III offer numerous advantages over the trihydrochloride salt and crystal. The 2.5 salt and Form II and Form III offer advantages to formulation and analytical development because they sorb less water overall over a wide range of relative humidity as compared to the trihydrochloride salt and crystal; they are thermodynamically more stable than the trihydrochloride salt and crystal; and they do not incorporate organic solvents as readily as the trihydrochloride salt and crystal.

The present invention provides a novel composition of matter: (2R)-anti-5-{3-[4-(10,11-difluoromethanodibenzosuber-5-yl)piperazin-1-yl]-2-hydroxypropoxy}quinoline 2.5 hydrochloride.

The present invention further provides a novel hydrate crystal form of (2R)-anti-5-{3-[4-(10,11-difluoromethanodibenzosuber-5-yl)piperazin-1-yl]-2-hydroxypropoxy}quinoline 2.5 hydrochloride ("Form II"), having an X-ray diffraction pattern comprising the following peaks: 6.0, 9.1, 10.8, 11.6, 12.0, 13.1, 13.6, 24.1, and 26.2±0.2° in 2θ when obtained with a copper radiation source.

The present invention further provides a novel hydrate crystal form of (2R)-anti-5-{3-[4-(10,11-difluoromethanodibenzosuber-5-yl)piperazin-1-yl]-2-hydroxypropoxy}quinoline 2.5 hydrochloride ("Form II"), having a solid-state $^{13}C$ NMR spectrum comprising isotropic peaks at the following chemical shifts: 29.9, 50.1, 55.3, 62.0, 66.5, 72.0, 75.8, 104.8, 107.5, 108.2, 109.1, 110.2, 112.0, 118.4, 119.5, 120.1, 123.1, 128.7, 131.1, 133.0, 134.8, 136.4, 136.9, 139.9, 140.0, 142.3, 144.5, 146.6, 149.0, 144.2, 153.0 and 153.6 ppm.

The present invention further provides a novel hydrate crystal form of (2R)-anti-5-{3-[4-(10,11-difluoromethanodibenzosuber-5-yl)piperazin-1-yl]-2-hydroxypropoxy}quinoline 2.5 hydrochloride ("Form III"), having an X-ray diffraction pattern comprising the following peaks: 8.2, 10.4, 11.9, 17.2, and 23.0±0.2° in 2θ when obtained with a copper radiation source.

The present invention further provides a novel hydrate crystal form of (2R)-anti-5-{3-[4-(10,11-difluoromethanodibenzosuber-5-yl)piperazin-1-yl]-2-hydroxypropoxy}quinoline 2.5 hydrochloride ("Form III"), having a solid-state $^{13}C$ NMR spectrum comprising isotropic peaks at the following chemical shifts: 30.3, 50.4, 59.1, 63.2, 72.8, 77.2, 109.1, 110.2, 112.2, 112.8, 118.7, 119.5, 119.9, 121.0, 122.2, 123.0, 128.9, 130.6, 132.7, 134.0, 136.4, 140.0, 141.0, 141.8, 142.5, 143.3, 146.1, 153.1, 153.8 and 154.7 ppm.

The present invention further provides a method of treatment for a drug resistant disease comprising coadministering to a mammal in need thereof a resistance modulating amount of the 2.5 hydrochloride salt, Form II, or Form III and an effective amount of a treatment drug for said drug resistant disease.

The present invention further provides a method of treatment for a multidrug resistant disease comprising coadministering to a mammal in need thereof a multidrug resistance modulating amount of the 2.5 hydrochloride salt, Form II or Form III and an effective amount of a treatment drag for said multidrug resistant disease.

The present invention further provides a method for enhancing bioavailability of a drug to the brain, comprising coadministering to a mammal in need thereof a therapeutically effective amount of said drug and the 2.5 hydrochloride salt, Form II, or Form III sufficient enough to allow said drug to cross the blood-brain barrier and enter the brain.

The present invention further provides a method for enhancing oral bioavailability of a drug comprising administering to a mammal in need thereof a therapeutically effective amount of said drug and the 2.5 hydrochloride salt, Form II, or Form III sufficient enough to allow said drug to be transported across the gastrointestinal tract and enter the bloodstream.

BRIEF DESCRIPTION OF THE FIGURES

FIG. 1 depicts a representative XRD pattern of Form II.
FIG. 2 depicts a representative XRD pattern of Form III.
FIG. 3 is a representative solid state $^{13}$C NMR spectrum of Form II.
FIG. 4 is a representative solid state $^{13}$C NMR spectrum of Form III.

DETAILED DESCRIPTION OF THE INVENTION

Definitions and General Parameters

The following definitions are set forth to illustrate and define the meaning and scope of the various terms used to describe the invention herein.

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D. C., "Pharmaceutical Salts", *J. Pharm. Sci.*, 66:1, 1977. Typical pharmaceutical salts include those salts prepared by reaction of the compounds of formula I with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "cancer therapeutic agent" refers to compounds, which have an anticancer therapeutic effect. Such compounds are non-antimetabolites such as anthracycline group antibiotics, e.g. adriamycin, daunomycin, doxorubicin, or aclasinomycin A; actinomycin group antibiotics, e.g. actinomycin C or D; chromomycin group antibiotics, e.g. mithramycin or toyomycin; vincoalkaloids, e.g. vincristine, or vinblastine; meitansins; podophyllotoxin derivatives, e.g. VP16-213; homoharintonin; angwindin; bruceantin; neocarcinostatin; anthromycin; mitomycin C; and cisplatin. Additional cancer therapeutic agents may be found in the medical literature, for example, Section Xi, "Chemotherapy of Neoplastic Diseases" in Goodman and Gilman's *The Pharmacological Basis of Therapeutics*, Seventh Edition, pages 1240-1306 (1985).

The term "bioavailability" refers to the degree and rate at which a drug, or other substance, becomes available to a target tissue within a mammal.

The term "coadministering" means a disease treatment drug and the 2.5 salt, Form II, or Form III are given to a mammal. The drug and the 2.5 salt, Form II, or Form III are given to a mammal simultaneously or at different times.

The term "drug resistance" refers to the circumstance when a disease does not respond to a treatment drug or drugs. Drug resistance can be either intrinsic, which means the disease has never been responsive to the drug or drugs, or it can be acquired, which means the disease ceases responding to a drug or drugs that the disease had previously responded to.

"Multidrug resistance" means a specific type of drug resistance characterized by cross-resistance of a disease to more than one functionally and/or structurally unrelated drugs. Multidrug resistance can be either intrinsic or acquired.

The terms and abbreviations used herein have their normal meanings unless otherwise designated, for example, "° C." refers to degrees Celsius; "N" refers to normal or normality; "mmol" refers to millimole or millimoles; "g" refers to gram or grams; "d" refers to density, "min." refers to minutes, "mL" means milliliter or milliliters; "M" refers to molar or molarity, "HPLC" refers to high performance liquid chromatography; "mm" refers to millimeters; "cm" refers to centimeters; "nm" refers to nanometers; and "$t_r$" refers to retention time.

Forms II and III offer significant advantages over the prior art compound Form I. For example Forms II and III have more favorable moisture sorption characteristics, i.e. a flatter moisture sorption profile, as they sorb less water overall over a wide range of relative humidity; Forms II and III are thermodynamically more stable than Form I, with Form II being the most stable in organic solutions and in the solid state at ambient temperature/relative humidity and Form III being the most stable in aqueous and acidic media; Forms II and III do not incorporate organic solvents as readily as Form I, eliminating the need for lengthy humidification steps which are required to remove residual organic solvents from the Form I lattice; and the crystal morphology of Forms II and III are superior to Form I for the purpose of bulk and pharmaceutical processing. Forms II and III have a distinctly different morphology, which has been shown to be easier to filter than the rod-shaped crystals of Form I.

A number of methods are available to characterize crystalline forms of organic compounds. Among these methods are differential scanning calorimetry, solid state NMR spectrometry, infra-red spectroscopy, and x-ray powder diffraction. The x-ray powder diffraction pattern, in particular, is very useful for distinguishing between different crystalline forms of a compound.

X-ray powder diffraction analysis can be readily performed as follows. After lightly grinding the sample with an agate mortar and pestle, the sample is loaded into a sample holder for the x-ray powder diffraction measurement. The x-ray powder diffraction patterns are measured using a Siemens D5000 x-ray powder diffractometer equipped with a CuKα source (λ=1.54056 Å). Forms II and III have typical XRD patterns as represented in Tables 1 and 2, respectively, with peaks which have typical relative intensities ($I/I_o$) at the following 2θ values, where θ is the incident angle of the X-ray beam. The error of measurement is +/−0.2° in 2θ. X-ray peaks with $I/I_o$ of 5% or greater were reported in Tables 1 and 2. The cutoff was chosen arbitrarily.

TABLE 1

Form II:

| Angle (°2θ) | I/I$_o$ (%) |
|---|---|
| 6.0 | 14.2 |
| 9.1 | 10.8 |
| 10.8 | 17.2 |
| 11.6 | 100 |
| 12.0 | 52.3 |
| 12.7 | 8.5 |
| 13.1 | 40.9 |
| 13.6 | 58 |
| 14.2 | 6 |
| 14.8 | 20.1 |
| 15.2 | 24.9 |
| 15.5 | 10.4 |
| 16.4 | 16 |
| 16.8 | 9.2 |
| 17.2 | 7.5 |
| 18.2 | 18.4 |
| 18.5 | 7.6 |
| 19.2 | 8.4 |
| 20.9 | 26.2 |
| 21.3 | 46.3 |
| 21.6 | 31.5 |
| 22.1 | 12.3 |
| 22.4 | 16.9 |
| 23.2 | 21.5 |
| 24.1 | 55.2 |
| 24.5 | 20.3 |
| 245.8 | 23.1 |
| 25.1 | 22.6 |
| 25.5 | 11.7 |
| 26.2 | 38.6 |
| 27.3 | 9.3 |
| 27.7 | 10.9 |
| 28.0 | 5.5 |
| 29.5 | 10.4 |
| 30.0 | 13.4 |
| 31.2 | 5.5 |
| 31.6 | 11.6 |

TABLE 2

Form III:

| Angle (°2θ) | I/I$_o$ (%) |
|---|---|
| 8.2 | 22.8 |
| 10.4 | 64.7 |
| 11.4 | 30.2 |
| 11.7 | 29.9 |
| 11.9 | 100 |
| 12.2 | 17.8 |
| 12.8 | 10.7 |
| 13.1 | 40.1 |
| 13.5 | 23.1 |
| 14.2 | 19.7 |
| 14.5 | 23.6 |
| 15.5 | 33.3 |
| 15.8 | 11.8 |
| 16.7 | 33.1 |
| 17.2 | 48 |
| 18.6 | 13.1 |
| 19.0 | 9 |
| 19.6 | 10.3 |
| 20.1 | 6.8 |
| 20.6 | 11.1 |
| 20.9 | 26.2 |
| 21.3 | 46 |
| 21.9 | 35.9 |
| 22.1 | 16.4 |
| 23.0 | 84.8 |
| 23.4 | 34.1 |
| 23.7 | 16.3 |
| 24.2 | 53.1 |

TABLE 2-continued

Form III:

| Angle (°2θ) | I/I$_o$ (%) |
|---|---|
| 24.7 | 32.8 |
| 25.5 | 30.1 |
| 26.1 | 12.6 |
| 26.5 | 18.2 |
| 26.7 | 12.8 |
| 27.2 | 10.4 |
| 28.7 | 6.1 |
| 29.3 | 5.4 |
| 29.8 | 5.8 |
| 30.1 | 9 |
| 30.7 | 5.4 |
| 31.2 | 5.2 |
| 31.4 | 6 |
| 32.0 | 5.9 |

It is well known in the crystallography art that, for any given crystal form, the relative intensities of the diffraction peaks may vary due to a number of factors, including the effects of preferred orientation which result from a particular crystal morphology, and particle size. Where the effects of preferred orientation and/or particle size are present, peak intensities (that is, the I/I$_o$ value) are altered, but the characteristic peak positions of the polymorph are unchanged. See, e.g., The United States Pharmacopoeia #23, National Formulary #18, pages 1843-1844, 1995. The effects of preferred orientation can be greatly reduced using a sample that is prepared in a manner that minimizes these effects, such as the use of a well ground sample.

Form II may be characterized as having an X-ray diffraction pattern which comprises peaks at the following 2θ values: 6.0, 9.1, 10.8, 11.6, 12.0, 13.1, 13.6, 24.1, and 26.2±0.2θ when measured using a copper radiation source.

Form III maybe characterized as having an X-ray diffraction pattern which comprises peaks at the following 2θ values: 8.2, 10.4, 11.9, 17.2, and 23.0±0.2° when measured using a copper radiation source.

Additionally, as the skilled artisan would appreciate, Form II and Form III may also be characterized by solid state NMR spectroscopy. Solid state $^{13}$C NMR spectra were collected with a Varian Unity 400 MHz spectrometer operating at a carbon frequency of 100.580 MHz, using high-power proton decoupling, cross polarization (CP) and magic angle spinning (MAS) at ~7.0 kHz. Acquisition parameters were as follows: 90° proton r.f. pulse width 4.0 µs, contact time 1.0 ms, pulse repetition time 5 s, spectral width 50 kHz, and acquisition time 50 ms. Chemical shifts, expressed as parts per million, were referenced to the methyl group of hexamethylbenzene (δ=17.3 ppm) by sample replacement. The magic angle was adjusted by optimizing the sidebands of the $^{79}$Br signal of KBr as described by Frye and Maciel Frye J. S. and Maciel G. E., *J. Magn. Reson.*, 1982, 48, 125).

Form II has a solid-state $^{13}$C NMR spectrum comprised of isotropic peaks at the following chemical shifts: 29.9, 50.1, 55.3, 62.0, 66.5, 72.0, 75.8, 104.8, 107.5, 108.2, 109.1, 110.2, 112.0, 118.4, 119.5, 120.1, 123.1, 128.7, 131.1, 133.0, 134.8, 136.4, 136.9, 139.9, 140.0, 142.3, 144.5, 146.6, 149.0, 144.2, 153.0 and 153.6 ppm.

Form III has a solid-state $^{13}$C NMR spectrum comprised of isotropic peaks at the following chemical shifts: 30.3, 50.4, 59.1, 63.2, 72.8, 77.2, 109.1, 110.2, 112.2, 112.8, 118.7, 119.5, 119.9, 121.0, 122.2, 123.0, 128.9, 130.6, 132.7, 134.0, 136.4, 140.0, 141.0, 141.8, 142.5, 143.3, 146.1, 153.1, 153.8 and 154.7 ppm.

TABLE 3

Chemical Shift Data and Peak Assignments for the Crystal Forms.

| Site | Form II | Form III |
|---|---|---|
| 1-4, 8-11, 25, 29 | 123.1, 128.7, 131.1, 133.0, 134.8 | 122.2, 123.0, 134.0 |
| 4A, 7A, 11A, 12A, 26A | 136.4, 136.9, 139.9, 140.0, 142.3, 144.2 | 128.9, 130., 132.7, 136.4, 140.0, 141.0, 141.8, 142.5 |
| 5, 7 | 29.9 | 30.3 |
| 6 | 112.0 | 112.8 |
| 12 | 75.8 | 77.2 |
| 14, 15, 17, 18 | 50.1 | 50.4 |
| 19 | 55.3 | 59.1 |
| 20, 21 | 62.0, 66.5, 72.0 | 63.2, 72.8 |
| 23 | 153.0, 153.6 | 153.1, 153.8, 154.7 |
| 24, 26 | 104.8, 107.5, 108.2, 109.1, 110.2, 112.0 | 109.1, 110.2, 112.2 |
| 28, 30 | 134.8, 144.5, 146.6, 149.0 | 134.0, 143.3, 146.1 |
| 30A | 118.4, 119.5, 120.1 | 118.7, 119.5, 119.9, 121.0 |

Additionally, as the skilled artisan would appreciate, Form II and Form III may also be characterized by the molar ratio of the chloride anion in the present invention. The determination can be analyzed by ion chromatography using a Dionex HPIC-AS4 with a Dionex Anion AMMS-1 micro-membrane suppressor. Using a standard stock solution of anhydrous sodium chloride (16.5 mg/100 ml), with standard concentration ranges from 50-150% of the chloride anion. The sample was prepared in a 1 mg/ml solution of purified water. Sonication for 10-15 min. and filtration was applied if insolubility was seen. A typical sample concentration of 0.1 mg/ml was used. The HPLC analysis conditions were conducted at 2 ml/min at room temperature with a run time of 780 sec. An approximate retention time of the chloride anion is about 115 sec. The molar percent of the anion was calculated by the following data analysis. A least squares calibration curve of the standard peak versus the standard peak concentration (μg/ml).

$$\text{anion } (\mu g/mL) = \frac{\text{Salt } wt. \text{ (mg)}}{100 \text{ mL}} \times \frac{\text{Anion } F.W.}{\text{Salt } F.W.} \times 1000 \text{ } (\mu g/mg) \times \text{dilution}$$

Determination of the anion concentration (μg/mL) in the sample solution was calculated from the observed peak area and the calibration curve.

$$\% \text{ anion} = (\mu g \text{ anion}/mL \text{ } found^*) \left[ \frac{mL \text{ } (samp.diluent)}{mg \text{ } (samp.weight)} \right] [\text{dilution}] \left[ \frac{1 \text{ mg}}{1000 \text{ } \mu g} \right] (100\%)$$

*from calibration curve

| Hydrate Form | Chloride (% w/w Anhydrous) | Molar ratio Cl⁻ |
|---|---|---|
| I | 16.20 | 2.94 |
| I | 17.00 | 3.06 |
| I | 16.85 | 3.06 |
| I | 16.92 | 3.10 |
| I | 17.01 | 3.09 |
| I | 16.46 | 2.91 |
| I | 16.14 | 2.89 |
| I | 16.75 | 2.99 |
| II | 13.52 | 2.44 |
| II | 14.36 | 2.52 |
| II | 13.82 | 2.54 |
| II | 13.73 | 2.47 |
| II | 14.16 | 2.54 |
| II | 14.05 | 2.56 |
| II | 13.88 | 2.46 |
| II | 14.31 | 2.55 |
| II | 14.11 | 2.51 |
| II | 13.99 | 2.47 |
| II | 14.09 | 2.46 |
| II | 14.91 | 2.61 |
| III | 13.97 | 2.46 |
| III | 13.74 | 2.43 |
| III | 13.87 | 2.45 |
| III | 13.56 | 2.37 |
| III | 14.56 | 2.56 |

The precise conditions under which Form II or Form III is formed may be experimentally determined and it is only possible to give a number of methods, which have been found to be suitable in practice. Thus, for example, Form II may be prepared by slurry conversion of Form III under controlled conditions. It is understood that the present process can utilize (2R)-anti-5-{3-[4-(10,11-difluoromethanodibenzosuber-5-yl)piperazin-1-yl]-2-hydroxypropoxy}quinoline trihydrochloride regardless of its hydration state or crystalline state. In particular, it can be prepared from (2R)-anti-5-{3-[4-(10,11-difluoromethanodibenzosuber-5-yl)piperazin-1-yl]-2-hydroxypropoxy}quinoline trihydrochloride. The skilled artisan is aware that it may be advantageous to add "seeds" of Form II or III to the solution in order to induce crystallization. Form II or III can be isolated from the crystallization solution by filtration, if desired after cooling, and washed and dried. If desired, either Form II or III may be further crystallized using similar conditions for crystallization to those described below.

The present invention is ether illustrated by the following examples and preparations. These examples and preparations are illustrative only and are not intended to limit the invention in any way. (2R)-anti-1-[4-(10,11-Difluoromethano-10,11-dihydro-5H-dibenzo[a,d]cyclohepten-5-yl)-piperazin-1-yl]-3-quinolin-5-yloxy)-propan-2-ol trihydrochloride may be prepared by any number of different methods as described in the art, see e.g. WO00/75121 and U.S. Pat. No. 5,654,304.

EXAMPLE 1

Form III

Suspend (2R)-anti-1-[4-(10,11-difluoromethano-10,11-dihydro-5H-dibenzo[a,d]cyclohepten-5-yl)-piperazin-1-yl]-3-quinolin-5-yloxy)-propan-2-ol trihydrochloride (502 mg) in 3A EtOH (10 mL). Heat to reflux and add $H_2O$ (5 mL) to dissolve the solids. Remove the heat source and add EtOAc (75 mL) to the warm solution. Isolate by vacuum filtration, wash with EtOAc (2 mL), and air-dry in a Büchner funnel under an air stream. Yield=415 mg.

EXAMPLE 2

Form III

Suspend (2R)-anti-1-[4(10,11-difluoromethano-10,11-dihydro-5H-dibenzo[a,d]cyclohepten-5-yl)-piperazin-1-yl]-3-quinolin-5-yloxy)-propan-2-ol trihydrochloride (1.53 g) in 15 mL of 8:1 IPA/$H_2O$, heat the suspension under reflux for 10-15 minutes to effect dissolution of the solids, and allow the solution to cool to room temperature to precipitate Form III. Allow the suspension to slurry overnight (~16 hrs), after which time isolate the solid product by vacuum filtration and wash with 10 mL IPA. Yield=1.14 g.

EXAMPLE 3

Form II

Suspend 7.52 g of (2R)-anti-1-[4-(10,11-difluoromethano-10,11-dihydro-5H-dibenzo[a,d]cyclohepten-5-yl)-piperazin-1-yl]-3-quinolin-5-yloxy)-propan-2-ol trihydrochloride in 6:1 v/v tert-butanol-water (75 mL) and heat under reflux for 30 minutes to dissolve the solids. Turn the heat source off, and allow the solution to slowly cool to room temperature. Observe a thick crystal slurry after 2 hours at 0° C., collect the solids by vacuum filtration, wash with ethyl acetate (50 mL), air-dry for ~6 hours and then dry in a 70° C. convection oven for 65 hours. Yield=5.33 g.

EXAMPLE 4

Form II

Suspend (2R)-anti-1-[4-(10,11-difluoromethano-10,11-dihydro-5H-dibenzo[a,d]cyclohepten-5-yl)-piperazin-1-yl]-3-quinoln-5-yloxy)-propan-2-ol trihydrochloride (506 mg) in 13 mL of 20:1 IPA/$H_2O$ and heat under reflux to dissolve the solids. Allow to cool to room temperature, during which time oily solid particles begin to precipitate from solution. Slurry the solid product for 24 hrs., and then isolate by vacuum filtration, wash with 5 mL IPA and air dry. Yield=310 mg.

EXAMPLE 5

Form II

Dry Form III at 50-70° C. in a convection oven.

The present invention further provides a method of treatment for a drug resistant disease comprising coadministering to a mammal in need thereof a resistance modulating amount of the 2.5 salt, Form II, or Form III and an effective amount of a treatment drug for said drug resistant disease. Preferably the disease is cancer. Preferably, the treatment drug is a cancer chemotherapeutic agent.

The present invention further provides a method of treatment for a multidrug resistant disease comprising coadministering to a mammal in need thereof a multidrug resistance modulating amount of the 2.5 salt, Form II, or Form III and an effective amount of a treatment drug for said multidrug resistant disease. Preferably, the treatment drug is a cancer chemotherapeutic agent.

The present invention further provides a method for enhancing bioavailability of a pharmaceutically active agent to the brain, comprising coadministering to a mammal in need thereof a therapeutically effective amount of said drug and the 2.5 salt, Form II, or Form III sufficient enough to allow said drug to cross the blood-brain barrier and enter the brain. Preferable the active agent is an HIV protease inhibitor. Examples of such protease inhibitors contemplated by the present invention are NELFINAVIR, which is preferably administered as the mesylate salt at 750 mg three times per day (U.S. Pat. No. 5,484,926, herein incorporated by reference); RITONAVIR, which is preferably administered at 600 mg twice daily (U.S. Pat. No. 5,484,801, herein incorporated by reference); SAQUINAVIR, which is preferably administered at the mesylate salt at 1,200 mg three times per day (U.S. Pat. No. 5,196,438, herein incorporated by reference); INDINAVIR, which is preferably administered as the sulfate salt at 800 mg three times per day (U.S. Pat. No. 5,413,999, herein incorporated by reference); and AMPRENAVIR, which is preferably administered at 1,200 mg twice daily (U.S. Pat. No. 5,585,397, herein incorporated by reference). The skilled artisan would recognize that this list is not exhaustive. Additionally, the skilled artisan would recognize that the protease inhibitors' administration to a patient may vary from the preferred.

The present invention further provides the use of the 2.5 salt, Form II, or Form III in combination with an effective amount of a treatment drug, or a pharmaceutically acceptable salt thereof, for the manufacture of a medicament for the treatment of a drug resistant disease. Preferably the disease is cancer. Preferably, the treatment drug is a cancer chemotherapeutic agent.

The invention further provides the use of the 2.5 salt, Form II, or Form III in combination with an effective amount of a treatment drug, or a pharmaceutically acceptable salt thereof, for the manufacture of a medicament for the treatment of a multidrug resistant disease. Preferably, the treatment drug is a cancer chemotherapeutic agent.

The present invention further provides the use of the 2.5 salt, Form II, or Form III in combination with a pharmaceutically active agent, or a pharmaceutically acceptable salt thereof, for the manufacture of a medicament for enhancing bioavailability of the pharmaceutically active agent to the brain, comprising coadministering to a mammal in need thereof a therapeutically effective amount of said drug and the 2.5 salt, Form II, or Form III sufficient enough to allow said drug to cross the blood-brain barrier and enter the brain. Preferably, the active agent is an HIV protease inhibitor.

Preferably, the present invention relates to a pharmaceutical formulation comprising the 2.5 salt, Form II, or Form III; one or more pharmaceutical carriers, diluents, or excipients; and optionally a treatment drug.

When employed as a pharmaceutical, the 2.5 salt, Form II, or Form III is usually administered in the form of pharmaceutical compositions. These compositions can be administered by a variety of routes including oral, rectal, transdermal, and intranasal. Such compositions are prepared in a manner well known in the pharmaceutical art and comprise the 2.5 salt, Form II, or Form III.

The term "substantially pure" refers to the crystal phase purity of Form II or III. In practice we have found that small amounts of other crystalline forms do not adversely affect the advantageous properties of Form II or III. According to the present invention substantially pure refers to Form II or III which is greater than 90%, preferably greater than 95% of the total crystalline material.

This invention also includes pharmaceutical compositions which contain the 2.5 salt, Form II, or Form III (referred to as "active ingredient" herein below) associated with pharmaceutically acceptable carriers. In making the compositions of this invention, the active ingredient is usually mixed with an excipient, diluted by an excipient or enclosed within such a carrier, which can be in the form of a capsule, sachet, paper or other container. When the excipient serves as a diluent, it can be a solid or semi-solid, which acts as a vehicle, carrier, or medium for the active ingredient. Thus, the compositions can be in the form of tablets, pills, powders, lozenges, sachets, cachets, emulsions, aerosols, ointments containing, for example, up to 10% by weight of the active compound, tablet, soft and hard gelatin capsules, suppositories, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 mg to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Preferably, the 2.5 salt, Form II, or Form III is employed at no more than about 20 weight percent of the pharmaceutical composition, more preferably no more than about 15 weight percent, with the balance being pharmaceutically inert carrier(s).

The 2.5 salt, Form II, or Form III is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing compositions such as tablets, the active ingredient is mixed with a pharmaceutical excipient to form a solid pre-formulation composition containing a homogeneous mixture of a compound of the present invention. When referring to these pre-formulation compositions as homogeneous, it is meant that the active ingredient is dispersed evenly throughout the composition so that the composition maybe readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include liquids, suspensions, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices, which deliver the formulation in an appropriate manner.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions, which can transiently open the blood-brain barrier.

Other suitable formulations for use in the present invention can be found in Remington's Pharmaceutical Sciences, Mace Publishing Company, Philadelphia, Pa., 17th ed. (1985).

As noted above, the 2.5 salt, Form II, or Form III is suitable for use in a variety of drug delivery systems described above. Additionally, in order to enhance the in vivo serum half-life of the present compound, it may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount of the 2.5 salt, Form II, or Form III administered to the patient will vary depending upon the purpose of the administration, such as prophylaxis or therapy, the state of the patient, the manner of administration, and the like. In therapeutic applications, compositions are administered to a patient already suffering from cancer in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of the disease state in the patient, the age, weight and general condition of the patient, and the like. Preferably, for use as therapeutics, the 2.5 salt, Form II or Form III is administered at dosages ranging from about 1 to about 500 mg/kg/day.

The present invention provides a process for preparing the Form II or Form III which comprises crystallizing (2R)-anti-5-{3-[4-(10,11-difluoromethanodibenzosuber-5-yl)piperazin-1-yl]-2-hydroxypropoxy}quinoline trihydrochloride from a solution of water and a water miscible solvent under conditions which yield Form II or III.

We claim:

1. A method of treatment for a drug resistant disease comprising coadministering to a mammal in need thereof a resistance modulating amount of a compound of the formula (2R)-anti-5-{3-[4-(10,11-difluoromethanodibenzosuber-5-yl) piperazin-1-yl]-2-hydroxypropoxy}quinoline 2.5 hydrochloride, and an effective amount of a treatment drug for said drug resistant disease, wherein the drug resistant disease is leukemia.

2. The method of claim 1, wherein the treatment drug is a cancer chemotherapeutic agent.

3. The method of claim 1, wherein the leukemia is multi-drug resistant.

4. The method of claim 3, wherein the resistance modulating amount is a multi-drug resistance modulating amount.

5. The method of claim 4, wherein the treatment drug is a cancer chemotherapeutic agent.

6. The method of claim 1, wherein the compound is crystalline.

7. The method of claim 6, wherein the crystalline compound has an X-ray diffraction pattern comprising peaks at the following 2θ values: 6.0, 9.1, 10.8, 11.6, 12.0, 13.1, 13.6, 24.1, and 26.2±0.2° when measured using a copper radiation source.

8. The method of claim 6, wherein the crystalline compound has an X-ray diffraction pattern comprising peaks at the following 2θ values: 8.2, 10.4, 11.9, 17.2, and 23.0±0.2° when measured using a copper radiation source.

* * * * *